US012569461B2

(12) United States Patent
Stramel et al.

(10) Patent No.: US 12,569,461 B2
(45) Date of Patent: Mar. 10, 2026

(54) THERAPEUTIC SUPPLEMENT

(71) Applicant: Manna Health LLC, San Diego, CA (US)

(72) Inventors: Rodney D. Stramel, San Diego, CA (US); Jeff Hill, San Diego, CA (US)

(73) Assignee: Manna Health LLC, San Diego, CA (US)

( * ) Notice: Subject to any disclaimer, the term of this patent is extended or adjusted under 35 U.S.C. 154(b) by 284 days.

(21) Appl. No.: 18/235,819

(22) Filed: Aug. 19, 2023

(65) Prior Publication Data

US 2024/0100007 A1 Mar. 28, 2024

Related U.S. Application Data

(60) Provisional application No. 63/410,965, filed on Sep. 28, 2022.

(51) Int. Cl.
| | |
|---|---|
| *A61K 9/127* | (2025.01) |
| *A61K 31/12* | (2006.01) |
| *A61K 31/201* | (2006.01) |
| *A61K 31/353* | (2006.01) |
| *A61K 47/10* | (2017.01) |
| *A61K 47/24* | (2006.01) |
| *A61K 47/34* | (2017.01) |
| *A61K 47/44* | (2017.01) |

(52) U.S. Cl.
CPC ............ *A61K 31/201* (2013.01); *A61K 9/127* (2013.01); *A61K 31/12* (2013.01); *A61K 31/353* (2013.01); *A61K 47/10* (2013.01); *A61K 47/24* (2013.01); *A61K 47/34* (2013.01); *A61K 47/44* (2013.01)

(58) Field of Classification Search
None
See application file for complete search history.

(56) References Cited

U.S. PATENT DOCUMENTS

2013/0017239 A1* 1/2013 Viladot Petit .......... A61K 8/342
424/401

* cited by examiner

*Primary Examiner* — Brian Gulledge
(74) *Attorney, Agent, or Firm* — Gordon Rees Scully & Mansukhani, LLP

(57) ABSTRACT

A self nanoemulsion drug delivery system (SNEDDS) may include a 10% quercetin SNEDD oil mixture including quercetin, oleic acid, castor oil and polyethylene glycol. The system also includes a microfluidized nanoliposomal solution including sunflower lecithin, glycerin and water. The oil mixture and nanoliposomal solution are combined to create a SNEDDS. The SNEEDS has a composition of about 1.00% by weight of quercetin and about 15.0% by weight of sunflower lecithin.

17 Claims, No Drawings

THERAPEUTIC SUPPLEMENT

CROSS-REFERENCE TO RELATED APPLICATION

This application claims priority to and the benefit of U.S. Provisional Patent Application No. 63/410,965, filed Sep. 28, 2022, which is incorporated by reference herein in its entirety.

DESCRIPTION

The present application discloses compositions and methods to prepare supplements of non-water soluble chemicals. For example, the application discloses supplements including curcumin or quercetin into nanoliposomal supplements to provide improved bio-availability.

Nanoliposome, or submicron bilayer lipid vesicle, is employed to encapsulate and deliver various bioactive agents or compounds. Some non-water soluble supplements (e.g., curcumin and quercetin) are difficult to be incorporated into nanoliposomes. The supplement particles are typically too large for the interior of the vesicle of the liposomes and too insoluble in the bilayer. There is a need for a solution to permit non-water soluble chemicals or compounds to be incorporated into nanoliposomes in order to take advantage of the improved bioavailability of nanoliposomes supplements. Particularly, there is a demand for a stable nanoliposomal product for non-water-soluble chemicals as supplements. The present application discloses such a solution and product.

The present application discloses a nanoliposomal supplement and method of making thereof, specifically nanoliposomal curcumin or nanoliposomal quercetin and method of making a supplement employing these compounds.

As disclosed herein, curcumin or quercetin is made into a self nanoemulsifying drug delivery system (SNEDDS) using oil (oleic acid), emulsifier (ETOCAS 35-LQ-RB or PEG-35 castor oil), cosolvent (PEG 400 or polyethylene glycol 400), and sunflower lecithin in water.

For the purpose of promoting an understanding of the principles of the disclosed compositions and methods, reference will now be made to embodiments illustrated herein and specific language will be used to describe the same. It will nevertheless be understood that no limitation of the scope of the invention is thereby intended. Any alterations and further modification in the described compositions, methods, products, and any further application of the principles of the invention as described herein, are contemplated as would normally occur to one skilled in the art to which the invention relates.

Conventional methods of emulsifying curcumin and quercetin include utilizing microfluidizers or high pressure homogenizers to create nanoparticles of curcumin and quercetin, but neither method can provide a stable nanoliposomal curcumin or nanoliposomal quercetin. The present disclosure discloses a method to create a stable nanoliposomal by introducing a unique oil and nanoliposomal sunflower lecithin mixture to create a SNEDDS of curcumin or quercetin.

The problem with conventional emulsifying methods is that these methods do not produce a yield of nano particles that is sufficient to develop a proper curcumin or quercetin based supplement. In addition, the curcumin and quercetin supplements produced using conventional methods do not result in enough bioavailability of curcumin and quercetin in the human body to provide the desired therapeutic benefits.

The method disclosed herein, employs an oil (oleic acid), an emulsifier (ETOCAS 35-LQ-RB or Castor Oil), a cosolvent (PEG 400), and a sunflower lecithin in water to create a SNEDDS curcumin or SNEDDS quercetin of improved stability and increased bioavailability.

Oleic acid is known to have high spontaneity for emulsification and high drug loading capacity (Venkatesh M, Mallesh K. *SELF-NANO EMULSIFYING DRUG DELIVERY SYSTEM (SNEDDS) FOR ORAL DELIVERY OF ATORVASTATIN-FORMULATION AND BIOAVAILABILITY STUDIES*). Castor oil and sunflower lecithin are also known as emulsifiers, along with PEG 400 as a cosolvent (Fida S, Jalil A, Habib R, Akhlaq M, Mahmood A, Minhas M U, et al. (2022) *Development of mucus-penetrating iodine loaded self-emulsifying system for local vaginal delivery.* PLoS ONE 17(3): e0266296. https://doi.org/10.1371/journal.pone.0266296 and Dammak, I, Sobral, PJdA, Aquino, A, Neves, MAd, Conte-Junior, C A. *Nanoemulsions: Using emulsifiers from natural sources replacing synthetic ones—A review.* Compr Rev Food Sci Food Saf. 2020; 19: 2721-2746. https://doi.org/10.1111/1541-4337.12606 and Varia S A, Faustino M M, Thakur A B, Clow C S, Serajuddin A T. *Optimization of cosolvent concentration and excipient composition in a topical corticosteroid solution.* J Pharm Sci. 1991 September; 80(9):872-5. doi: 10.1002/jps.2600800914. PMID: 1800711). The foregoing references are incorporated by reference herein.

Thus, although oleic acid, castor oil, PEG 400, and sunflower lecithin have been utilized separately in drug delivery systems there has been no indication that would demonstrate that the combination of these compounds would result in the high quality SNEDDS disclosed herein.

An exemplary embodiment of a self nanoemulsion drug delivery system (SNEDDS) including quercetin is disclosed. The SNEDDS includes a 10% quercetin SNEDD oil mixture including quercetin, oleic acid, castor oil and polyethylene glycol, a microfluidized nanoliposomal solution including sunflower lecithin, glycerin and water, the oil mixture and nanoliposomal solution are combined to create a SNEDDS having a composition of about 0.2% by weight oleic acid, about 3.8% by weight of castor oil, about 5.0% by weight of polyethylene glycol. about 1.00% by weight of quercetin, about 15.0% by weight of sunflower lecithin, about 2.70% by weight of glycerin, and about 72.0% by weight of water.

Also, an exemplary embodiment, a self nanoemulsion drug delivery system (SNEDDS) including curcumin is disclosed. The SNEDDS includes a 10% curcumin SNEDD oil mixture including quercetin, oleic acid, castor oil and polyethylene glycol, a microfluidized nanoliposomal solution including sunflower lecithin, glycerin and water, the oil mixture and nanoliposomal solution are combined to create a SNEDDS having a composition of about 0.2% by weight oleic acid, about 3.8% by weight of castor oil, about 5.0% by weight of polyethylene glycol, about 1.00% by weight of quercetin, about 15.0% by weight of sunflower lecithin, about 2.70% by weight of glycerin, and about 72.0% by weight of water.

An exemplary method of making a self nanoemulsion drug delivery system (SNEDDS) is also disclosed herein. The method comprising the steps of preparing a 10% quercetin SNEDD oil mixture by mixing a substance, oleic acid, castor oil and polyethylene glycol, wherein the substance is curcumin or quercetin, preparing a microfluidized nanoliposomal solution including sunflower lecithin, glycerin and water. Combining the oil mixture and nanoliposomal to create a SNEDDS having a composition of about 0.2% by weight oleic acid, about 3.8% by weight of castor oil, about 5.0% by weight of polyethylene glycol, about 1.00% by weight of quercetin, about 15.0% by weight of sunflower lecithin, about 2.70% by weight of glycerin and about 72.0% by weight of water.

The specific solution discussed above includes the following exemplary steps. An oil mixture comprising a mix of following compounds found in Table 1 is prepared.

TABLE 1

| Oil Mixture Composition | |
| --- | --- |
| Component | Weight (g) |
| Oleic Acid | 1 |
| PEG 35 Castor Oil | 20 |
| PEG 400 | 26 |

Then 1.4 g of quercetin or curcumin is mixed with 12.6 g of the oil mixture shown in Table 1 and warmed to 50° C. This results in a 10% (by weight) quercetin or curcumin SNEDD oil mixture (i.e., 1.4 g of quercetin (or curcumin) in a 14 g SNEDD oil mixture). A sunflower nanoliposomal mixture comprising a mix of the following compounds shown in Table 2 is prepared.

TABLE 2

| Sunflower Nanoliposomal Mixture Composition | |
| --- | --- |
| Component | Weight (g) |
| Sunflower Lecithin | 16.70 |
| Glycerin | 3.00 |
| USP Water | 80.30 |

The sunflower nano is microfluidized via a homogenizer at 30000 psi yielding a nanoliposomal solution. The sunflower nanoliposomal mixture is then combined with the quercetin/curcumin SNEDD oil mixture above to provide the SNEDDS.

The preparation above results in a curcumin and quercetin SNEDDS with the following characteristics and distribution:

TABLE 3

| SNEDDS Characteristics | | | | | |
| --- | --- | --- | --- | --- | --- |
| | Mv | Mn | Ma | D50 | D95 |
| SNEDDS 200 mg quercetin in 20 mL nanoliposomal sunflower lecithin | 51 nm | 29 nm | 35 nm | 34 nm | 120 nm |
| SNEDDS 200 mg curcumin in 20 mL nanoliposomal sunflower lecithin | 51 nm | 34 nm | 41 m | 41 m | 113 nm |

Mv = Volume mean diameter (De Brouckere Mean Diameter).
Mn = Number mean diameter.
Ma = Surface area mean dimeter (Sauter Mean Diameter).
D50 = 50$^{th}$ percentile diameter.
D95 = 95$^{th}$ percentile diameter.

Volume mean diameter (Mv, De Brouckere Mean Diameter, or D[4,3]) is the is the mean of a particle size distribution weighted by the volume.

Number mean diameter (Mn, or D[1,0]) is the average diameter of the particle per the number of particles.

Surface area mean dimeter (Ma, Sauter Mean Diameter, or D[3,2]) is the mean diameter with the same volume to surface area ratio as the sample.

The SNEDDS shown above in table 3 include 2 grams of the 10% quercetin/curcumin SNEDDS mixture with 18 g of the Sunflower Nanoliposomal Mixture Composition. The resulting % weight of the final composition is shown in Table 4 below.

TABLE 4

| Final Solution By % Weight | |
| --- | --- |
| Component | % (by weight) |
| Oleic Acid | 0.191 |
| PEG 35 Castor Oil | 3.83 |
| PEG 400 | 4.98 |
| Quercetin/Curcumin | 1.00 |
| Sunflower Lecithin | 15.03 |
| Glycerin | 2.70 |
| USP Water | 72.27 |

The SNEDDS characteristics shown in table 3 are uniquely related to the process and compositions of the mixture disclosed above. The resulting process creates particles are smaller than achieved with previous methods. Prior art methods dispersed the solid curcumin or quercetin particles. It was not possible to obtain mean particle size less than 100 nm dispersing the solid particles.

Below is a brief description of each ingredient shown in Table 4, along with their respective uses and benefits in relation to the inventive composition.

Oleic acid is a monounsaturated fatty acid and acts as an emulsifier, assisting in the formation of stable emulsions. This leads to enhanced solubilization and bioavailability of the quercetin or curcumin.

PEG 35 castor oil is a polyethylene glycol derivative of castor oil is used as an emulsifier. It possesses excellent emulsifying properties, enabling the formation of stable oil-in-water emulsions. Castor oil aids in the bioavailability of quercetin or curcumin.

PEG 400 is another polyethylene glycol that is used as a co-solvent. It improves drug loading capacity and bioavailability of quercetin or curcumin by reducing particle size and increasing solubility.

Sunflower lecithin is another emulsifier that is configured to help stabilize the compound.

Glycerin aids in maintaining moisture within the compound.

Quercetin and curcumin are naturally occurring polyphenolic compounds. They are renowned for their antioxidant, anti-inflammatory, and anticancer properties. However, due their relatively poor water solubility the bioavailability of quercetin and curcumin may be limited. However, the compound formulation disclosed herein aims to address this limitation, thus enabling better absorption and distribution of quercetin and/or curcumin in the body.

According to another embodiment, a self nanoemulsion drug delivery system (SNEDDS) is disclosed herein. The SNEDDS preferably includes the following components at the range specified below:

a 10% (8 to 12%) quercetin SNEDD oil mixture with a sunflower lecithin nanoliposomal solution; wherein the SNEDD oil mixture and the sunflower lecithin nanoliposomal solution creates a mixture having the composition of about 0.2% (0.18 to 0.22%) by weight oleic acid;

about 4.0% (3.6 to 4.4%) by weight of castor oil;

about 5.0% (4.8 to 5.2%) by weight of polyethylene glycol;

about 1.0% (0.8 to 1.2%) by weight of quercetin or curcumin;

about 15.0% (14.8 to 15.2%) by weight of sunflower lecithin;

about 2.70% (2.4 to 3.0%) by weight of glycerin; and about 72% (70.0 to 74%) by weight of water.

According to another embodiment, a self nanoemulsion drug delivery system (SNEDDS) is disclosed herein. The SNEDDS preferably includes the following components at the range specified below:

a 10% (8 to 12%) quercetin SNEDD oil mixture with a sunflower lecithin nanoliposomal solution; wherein the SNEDD oil mixture and the sunflower lecithin nanoliposomal solution creates a mixture having the composition of about 0.2% (0.18 to 0.22%) by weight oleic acid;

about 4.0% (3.6 to 4.4%) by weight of castor oil;

about 5.0% (4.8 to 5.2%) by weight of polyethylene glycol;

about 1.0% (0.8 to 1.2%) by weight of quercetin or curcumin;

about 15.0% (14.8 to 15.2%) by weight of sunflower lecithin;

about 2.70% (2.4 to 3.0%) by weight of glycerin; and about 72% (70.0 to 74%) by weight of water.

According to yet another embodiment, the SNEDDS consists essentially of:

a 10% (8 to 12%) quercetin SNEDD oil mixture with a sunflower lecithin nanoliposomal solution; wherein the SNEDD oil mixture and the sunflower lecithin nanoliposomal solution creates a mixture consisting essentially of about 0.2% (0.18 to 0.22%) by weight oleic acid;

about 4.0% (3.6 to 4.4%) by weight of castor oil;

about 5.0% (4.8 to 5.2%) by weight of polyethylene glycol;

about 1.0% (0.8 to 1.2%) by weight of quercetin or curcumin;

about 15.0% (14.8 to 15.2%) by weight of sunflower lecithin;

about 2.70% (2.4 to 3.0%) by weight of glycerin; and about 72% (70.0 to 74%) by weight of water.

Although PEG 400 is used in the embodiments described above other cosolvents may be used such as PEG 200, PEG 300, PEG 500, PEG 600. Additionally other polyethoxylated castor oils may be utilized instead of PEG 35 Castor Oil.

All publications disclosed herein are incorporated by reference to the same extent as if each individual publication was specifically and individually indicated to be incorporated by reference. It is to be understood that while a certain form of the invention is described, it is not intended to be limited to the specific form or arrangement herein described. It will be apparent to those skilled in the art that various changes may be made without departing from the scope of the invention and the invention is not to be considered limited to what is shown and described in the specification.

One skilled in the art will readily appreciate that the present invention is well adapted to carry out the objectives and obtain the ends and advantages mentioned, as well as those inherent therein. The compositions, formulations, methods, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention are intended to be within the scope of the invention.

What is claimed is:

1. A self nanoemulsion drug delivery system (SNEDDS) comprising:

a 10% quercetin SNEDD oil mixture including quercetin, oleic acid, castor oil and polyethylene glycol;

a microfluidized nanoliposomal solution including sunflower lecithin, glycerin and water;

wherein the oil mixture and nanoliposomal solution are combined to create a SNEDDS having a composition of:

about 0.2% by weight oleic acid;

about 3.8% by weight of castor oil;

about 5.0% by weight of polyethylene glycol;

about 1.00% by weight of quercetin;

about 15.0% by weight of sunflower lecithin;

about 2.70% by weight of glycerin; and about 72.0% by weight of water.

2. The SNEEDS of claim 1, wherein the volume mean diameter of the SNEEDS is about 51 nm.

3. The SNEEDS of claim 1, wherein the number mean diameter of the SNEEDS is about 29 nm.

4. The SNEEDS of claim 1, wherein the surface mean diameter of the SNEEDS is about 35 nm.

5. The SNEEDS of claim 1, wherein the mean particle size of the SNEEDS is less than 100 nm.

6. A self nanoemulsion drug delivery system (SNEDDS) comprising:

a 10% curcumin SNEDD oil mixture including curcumin, oleic acid, castor oil and polyethylene glycol;

a microfluidized nanoliposomal solution including sunflower lecithin, glycerin and water;

wherein the oil mixture and nanoliposomal solution are combined to create a SNEDDS consisting essentially of:

about 0.2% by weight oleic acid;

about 3.8% by weight of castor oil;

about 5.0% by weight of polyethylene glycol;

about 1.00% by weight of curcumin;

about 15.0% by weight of sunflower lecithin;

about 2.70% by weight of glycerin; and about 72.0% by weight of water.

7. The SNEEDS of claim 6, wherein the volume mean diameter of the SNEEDS is about 51 nm.

8. The SNEEDS of claim 1, wherein the number mean diameter of the SNEEDS is about 29 nm.

9. The SNEEDS of claim 1, wherein the surface mean diameter of the SNEEDS is about 35 nm.

10. The SNEEDS of claim 1, wherein the mean particle size of the SNEEDS is less than 100 nm.

11. A method of making a self nanoemulsion drug delivery system (SNEDDS) comprising the steps of:

preparing a 10% curcumin SNEDD oil mixture by mixing a substance, oleic acid, castor oil and polyethylene glycol;

wherein the substance is curcumin or quercetin;

preparing a microfluidized nanoliposomal solution including sunflower lecithin, glycerin and water;

combining the oil mixture and nanoliposomal to create a SNEDDS having a composition of about 0.2% by weight oleic acid;

about 3.8% by weight of castor oil;

about 5.0% by weight of polyethylene glycol;

about 1.00% by weight of curcumin;

about 15.0% by weight of sunflower lecithin;

about 2.70% by weight of glycerin; and about 72.0% by weight of water.

12. The method of claim 11, wherein the preparation of the 10% curcumin SNEED oil mixture is made by warming up the oleic acid, castor oil and polyethylene glycol.

13. The method of claim 11, wherein the microfluidized nanoliposomal solution is made by utilizing a homogenizer at 30000 psi.

14. The method of claim 11, wherein the volume mean diameter of the SNEEDS is about 51 nm.

15. The method of claim 11, wherein the number mean diameter of the SNEEDS is about 29 nm.

16. The method of claim 11, wherein the surface mean diameter of the SNEEDS is about 35 nm.

17. The method of claim 11, wherein the mean particle size of the SNEEDS is less than 100 nm.

\* \* \* \* \*